US00PP09284P

United States Patent [19]

Machin

[11] Patent Number: Plant 9,284

[45] Date of Patent: Sep. 12, 1995

[54] CHRYSANTHEMUM PLANT NAMED 'DARK ENAMOUR'

[75] Inventor: Barrie J. Machin, Hants, England

[73] Assignee: Goldstock Breeding Limited, Hants, England

[21] Appl. No.: 254,054

[22] Filed: Jun. 3, 1994

[51] Int. Cl.[6] ..... A01H 5/00

[52] U.S. Cl. ..... Plt./74.1

[58] Field of Search ..... Plt. 74.1, 82.4

[56] References Cited

U.S. PATENT DOCUMENTS

| | | | |
|---|---|---|---|
| P.P. 8,058 | 12/1992 | Vanden Berg | Plt./74.1 |
| P.P. 8,802 | 6/1994 | Polys | Plt./74.1 |
| P.P. 8,808 | 6/1994 | Vanden Berg | Plt./82.4 |
| P.P. 8,829 | 7/1994 | Vanden Berg | Plt./74.1 |
| 4,616,099 | 10/1986 | Sparkes | 47/58 |

OTHER PUBLICATIONS

Broertjes, et al., 1980, "A Mutant of a Mutant of a . . . Irradiation of Progressive Radiation-Induced Mutants in a Mutation Breeding Programme with *Chrysanthemum morifolium*", Euphytica, 29:526-530.

Gosling, ed., 1979, "The Chrysanthemum Manual-6th Edition", The National Chrysanthemum Society, London, Essex Telegraph Press, Ltd., pp. 329-336.

Broertjes, et al., 1978, "Application of Mutation Breeding Methods In the Improvement of Vegetatively Propagated Crops", Elsevier Sci. Pub. Co., New York, pp. 162-175.

Searle, et al., 1968, "Chrysanthemums the Year Round", Blanford Press, London, pp. 27-29, 320-327.

Chan, 1966, "Chrysanthemum and Rose Mutations Induced by X-Rays", Am. Soc. Hort. Sci. Proc., pp. 613-620.

Broertjes, 1966, "Mutation Breeding of Chrysanthemums", Euphytica, 15:156-162.

Dowrick, et al., 1966, "The Induction of Mutatins in Chrysanthemum Using X- and Gamma Radiation", Euphytica, 15:204-210.

*Primary Examiner*—Howard J. Locker

*Attorney, Agent, or Firm*—Foley & Lardner

[57] ABSTRACT

A new Chrysanthemum cultivar named Dark Enamour characterized by the combined features of cup-shaped capitulum form, daisy capitulum type, lavender-purple ray floret color, capitulum diameter of 5-6 cm, a plant height of 105 cm, a response period of 50-53 days when grown with 14 long days prior to start of short days, and an inverted pyramid flower formation.

3 Drawing Sheets

The present invention comprises a new and distinct cultivar of Chrysanthemum, botanically known as *Dendranthema grandiflora,* and referred to by the cultivar name Dark Enamour.

Dark Enamour is a mutation of Enamour which originated from a cross made by the inventor Dr. Barrie J. Machin, in a controlled breeding program in Fareham, England in 1987. The parent cultivar is disclosed in pending application Ser. No. 08/254,265.

Dark Enamour is a product of a mutation induction program carried out by the inventor in Fareham, England. The program had the objective of creating new cultivars that would expand the ray floret color range of Enamour, which has very light pink ray floret color.

Dark Enamour was discovered and selected by Barrie J. Machin in August 1989 in Wareham, England as one flowering plant within a flowering block established as rooted cuttings from plants of Enamour that had been exposed as unrooted cuttings to an x-ray source of 1500 rods.

The first act of asexual reproduction of Dark Enamour was accomplished when vegetative cuttings were taken from the initial selection in October 1989 in a controlled environment in Fareham, England by Dr. Barrie J. Machin.

Horticultural examinations of controlled flowerings of successive plantings has shown that the unique combination of characteristics as herein disclosed for Dark Enamour are firmly fixed and are retained through successive generations of asexual reproduction.

Dark Enamour has not been observed under all possible environmental conditions. The phenotype may vary somewhat with variations in environment such as temperature, light intensity and day length, without, however, any variance in genotype.

The following observations, measurements and comparisons describe plants grown in Fareham, England under greenhouse conditions which approximate those generally used in commercial greenhouse practice.

The following traits have been repeatedly observed and are determined to be basic characteristics of Dark Enamour which in combination distinguish this Chrysanthemum as a new and distinct cultivar.

1. Cup-chaped cupitulum form.
2. Daisy capitulum type.
3. Lavender-purple ray floret color.
4. Diameter across face of capitulum og 5-6 cm when fully open.
5. Flowering response under normal temperatures is 50 to 53 after start of short days.
6. Peduncle length of the first lateral at flowering after removal of the apical bud and without growth regulator applications is 10 cm; peduncle length of the fourth lateral at flowering is 12 cm.
7. Plant height of 105 cm.

The accompanying photographic drawings show typical inflorescence and leaf characteristics of Dark Enamour, with the colors being as nearly true as possible with illustrations of this type.

The color photograph on sheet 1 illustrates flowers and foliage of Dark Enamour grown as a cut spray mum. It should be noted that the illustrated ray floret color is much pinker than the lavender-purple (75B)

true flower color of Dark Enamour, due to imperfections in the photographic process.

The black and white photo on sheet 2 illustrates three views of the inflorescence of Dark Enamour.

The black and white photo on sheet 3 shows the upper and under surfaces of the leaves of Dark Enamour at three stages of development.

Of cultivars known to the inventor, the most similar in comparison to Dark Enamour is the parent cultivar Enamour. Reference is made to the attached chart A which compares certain characteristics of Dark Enamour with the same characteristics of Enamour. Although there are minor differences in flowering response and plant height, the main difference is ray floret color. The ray floret color of Enamour is a very light pink (red-purple 65C) compared to the generally lavender-purple ray floret color (75B) of Dark Enamour.

In the following description, color references are made to The Royal Horticultural Society Colour Chart. The color values were determined on plant material grown as a single spray cut mum in Fareham, England in 1989.

Classification:

*Botanical.*—*Dendranthema grandiflora* cv Dark Enamour.

*Commercial.*—Single spray cut mum.

Inflorescence

A. Capitulum:

*Form.*—Cup-shaped.

*Type.*—Daisy.

*Diameter across face.*—5–6 cm.

B. Corolla of ray florets:

*Color (generally).*—lavender-purple.

*Color (upper surface).*—75B.

*Color (under surface).*—75C.

*Shape.*—Long, pointed and flat.

C. Corolla of disc florets:

*Color (mature).*—13A.

*Color (immature).*—153C.

*Diameter.*—Approximately 15 mm.

D. Reproductive organs:

*Androecium.*—Present only on disc florets; no pollen present.

*Gynoecium.*—Present in disc and ray florets.

Plant

A. General appearance:

*Height.*—105 cm.

*Branching pattern.*—Regular branching habit, typically one branch developing per leaf axil.

B. Foliage:

*Color (upper surface).*—R.H.S. 147A.

*Color (under surface).*—R.H.S. 147B.

*Shape.*—Pinnately lobed with deep marginal indentations; see photo on sheet 3.

CHART A

| CHARACTERISTICS | DARK ENAMOUR | ENAMOUR |
|---|---|---|
| Ray floret color | Lavender-purple | Pink |
| Capitulum form and type | cup-shaped, daisy | cup-shaped, daisy |
| Diameter across face of capitulum | 5–6 cm | 5–6 cm |
| Flowering response | 50–53 days | 49–52 days |
| Plant height | 105 cm | 110 cm |
| Peduncle length | | |
| 1st lateral | 10 cm | 11 cm |
| 4th lateral | 12 cm | 13 cm |
| Spray formation | Columnar | Columnar |

It is claimed:

1. A new and distinct Chrysanthemum plant named Dark Enamour, as described and illustrated.

* * * * *

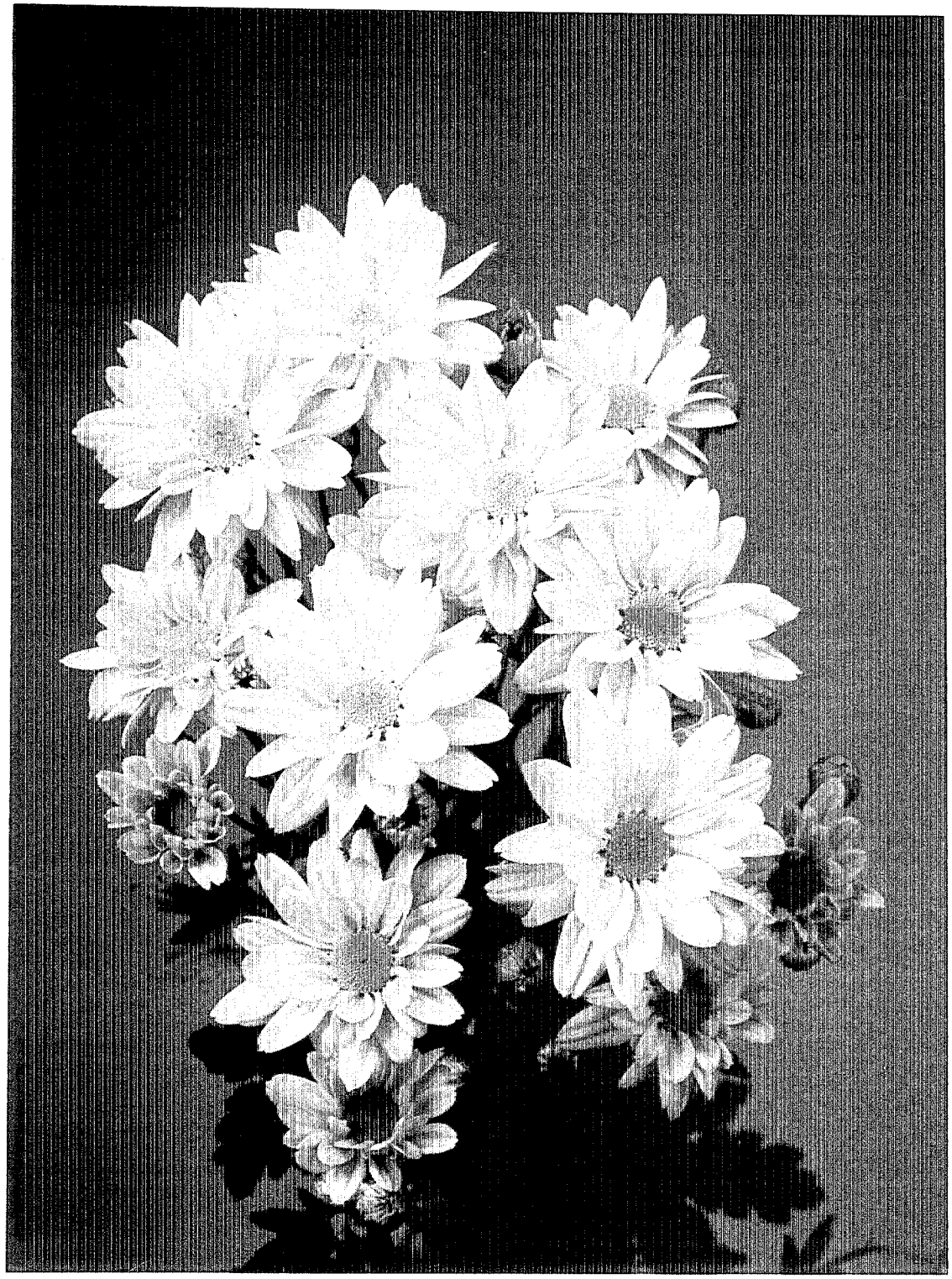

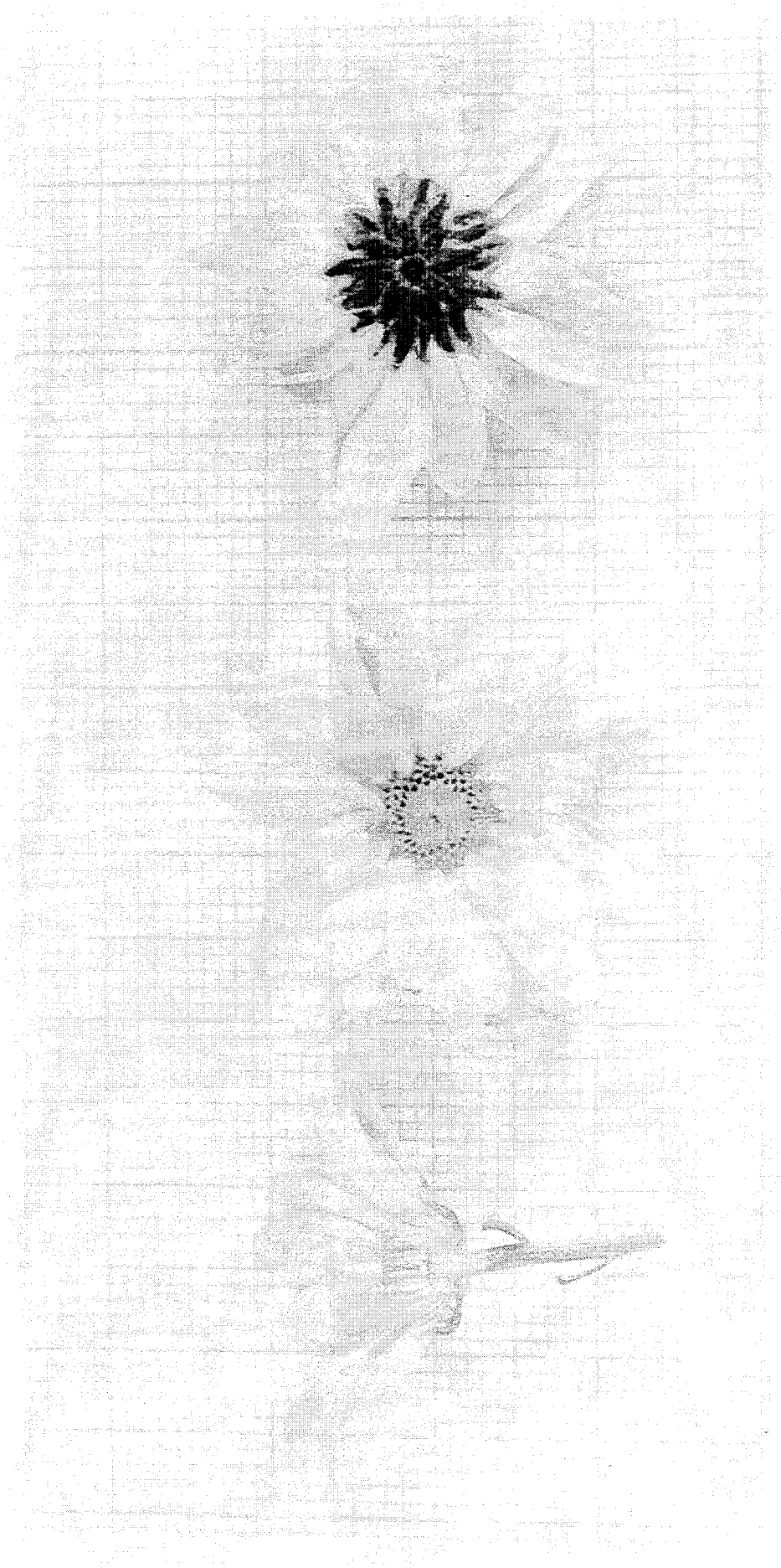

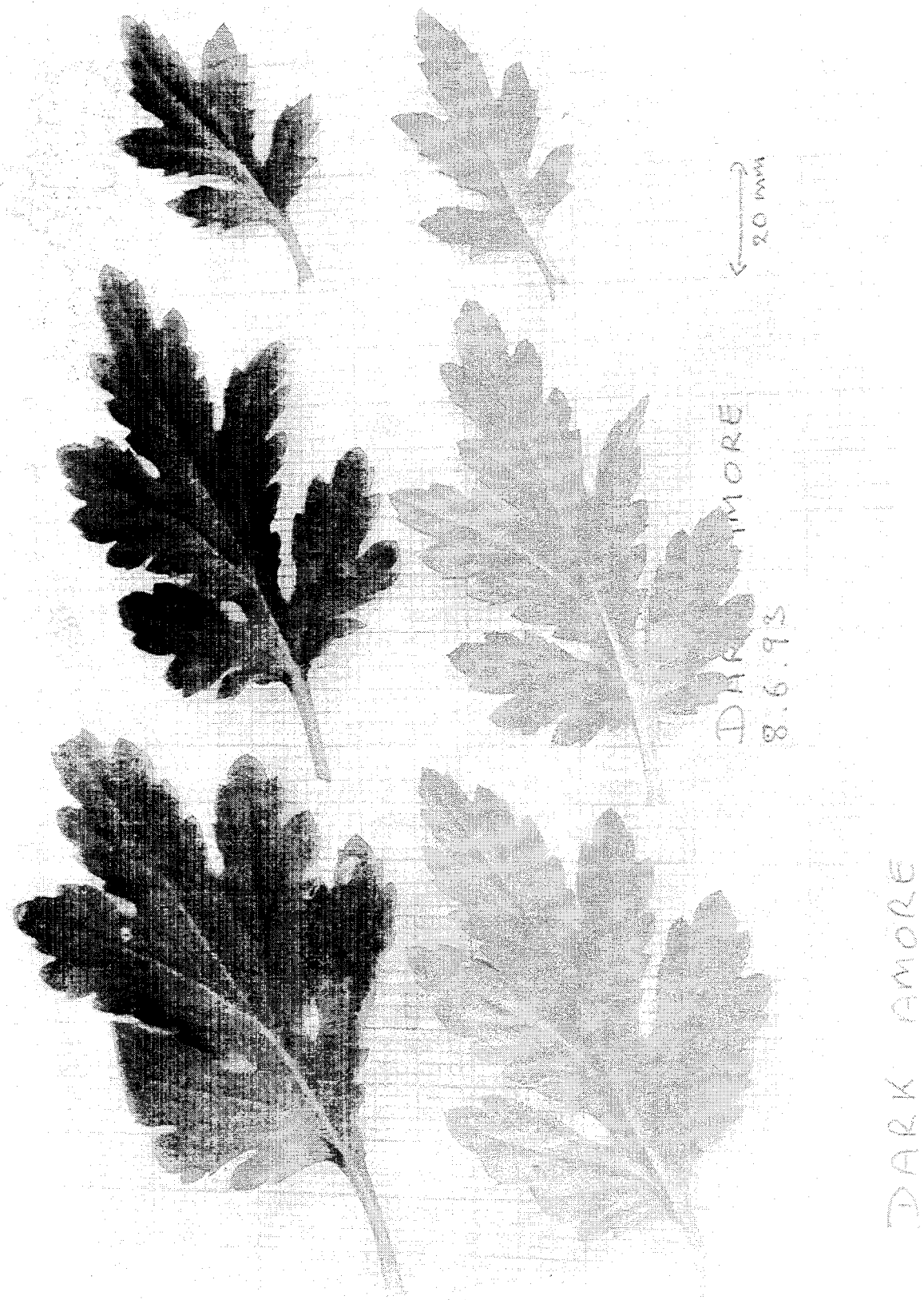
20 mm
DARK AMORE
8.6.93
DARK AMORE